United States Patent [19]
Kiro

[11] Patent Number: 5,634,885
[45] Date of Patent: Jun. 3, 1997

[54] TONGUE DEPRESSOR WITH LOLLIPOP HOLDER

[76] Inventor: Amnon Kiro, 28 Yirmiyahu, 44342 Kfar Saba, Israel

[21] Appl. No.: 506,753

[22] Filed: Jul. 26, 1995

[30] Foreign Application Priority Data

Mar. 29, 1995 [IL] Israel .......................... 113182

[51] Int. Cl.$^6$ ........................................ A61B 11/02
[52] U.S. Cl. ........................................ 600/240; 426/134
[58] Field of Search .................. 600/240, 239; 426/104, 134; D1/127, 102; D24/135, 136

[56] References Cited

U.S. PATENT DOCUMENTS

| | | | |
|---|---|---|---|
| 1,502,006 | 7/1924 | Alvord | 426/134 |
| 1,586,137 | 5/1926 | Zanath . | |
| 1,618,324 | 2/1927 | Burt . | |
| 1,847,415 | 3/1932 | Snell | D1/127 |
| 1,867,945 | 7/1932 | Hunter | 426/134 |
| 2,085,330 | 6/1937 | Price | 99/137 |
| 2,425,945 | 8/1947 | Leach . | |
| 2,653,597 | 9/1953 | Canan . | |
| 2,857,908 | 10/1958 | Cornfield . | |
| 3,324,849 | 6/1967 | Kravitz . | |
| 3,349,764 | 10/1967 | Edinger et al. | D24/136 |
| 3,615,596 | 10/1971 | Petti . | |
| 3,867,927 | 2/1975 | Hergott . | |

*Primary Examiner*—Richard J. Apley
*Assistant Examiner*—Beverly M. Flanagan
*Attorney, Agent, or Firm*—Mark M. Friedman

[57] ABSTRACT

A tongue depressor which includes a blade and a holder. One end of the blade functions as a conventional tongue depressor. The other end of the blade accommodates the holder which functions to receive and grasp the stick of a lollipop. In another configuration, the tongue depressor includes a blade for restraining the tongue of the patient, the blade being formed with a slot shaped to accommodate the stick of the lollipop.

14 Claims, 2 Drawing Sheets

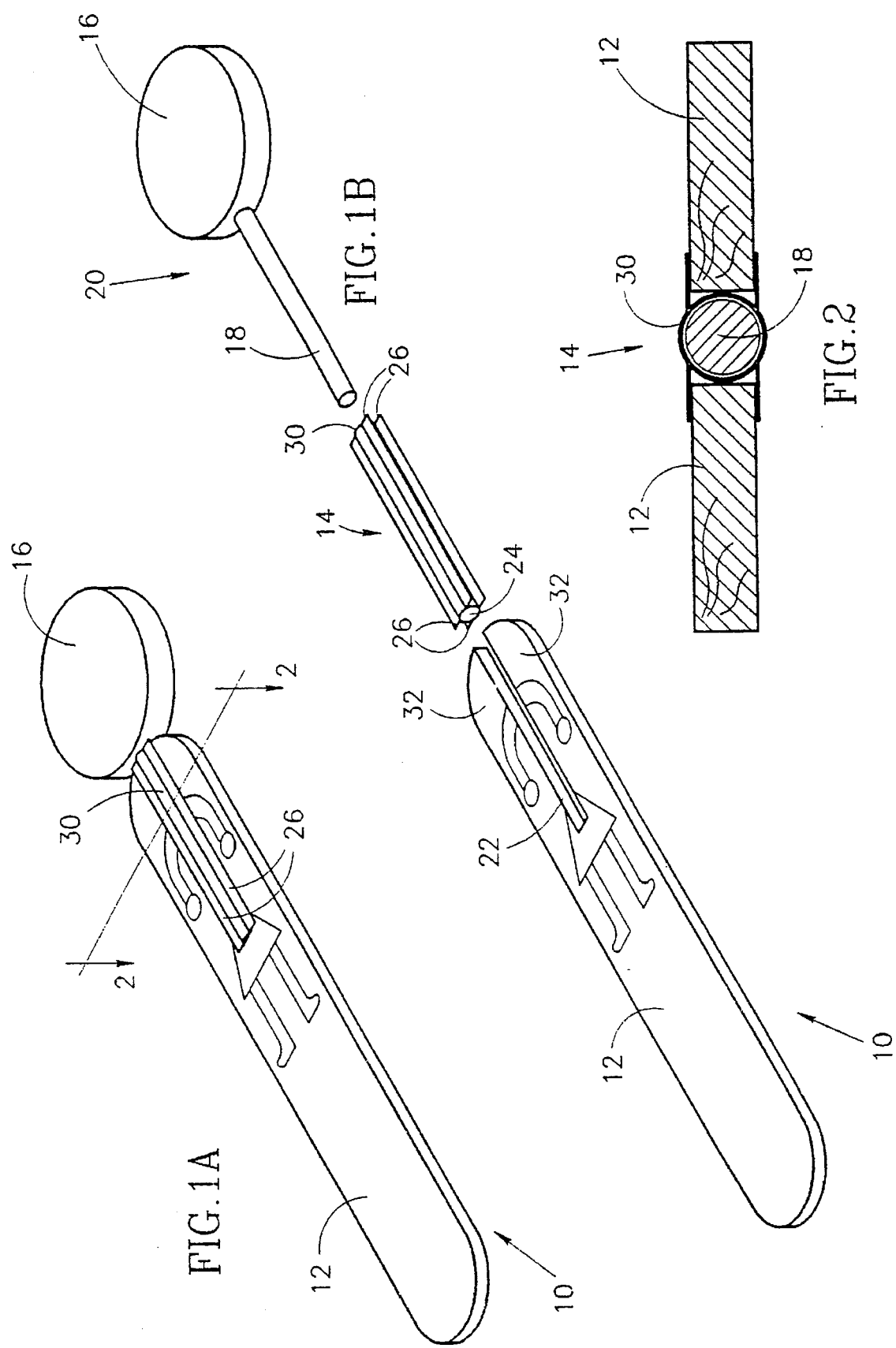

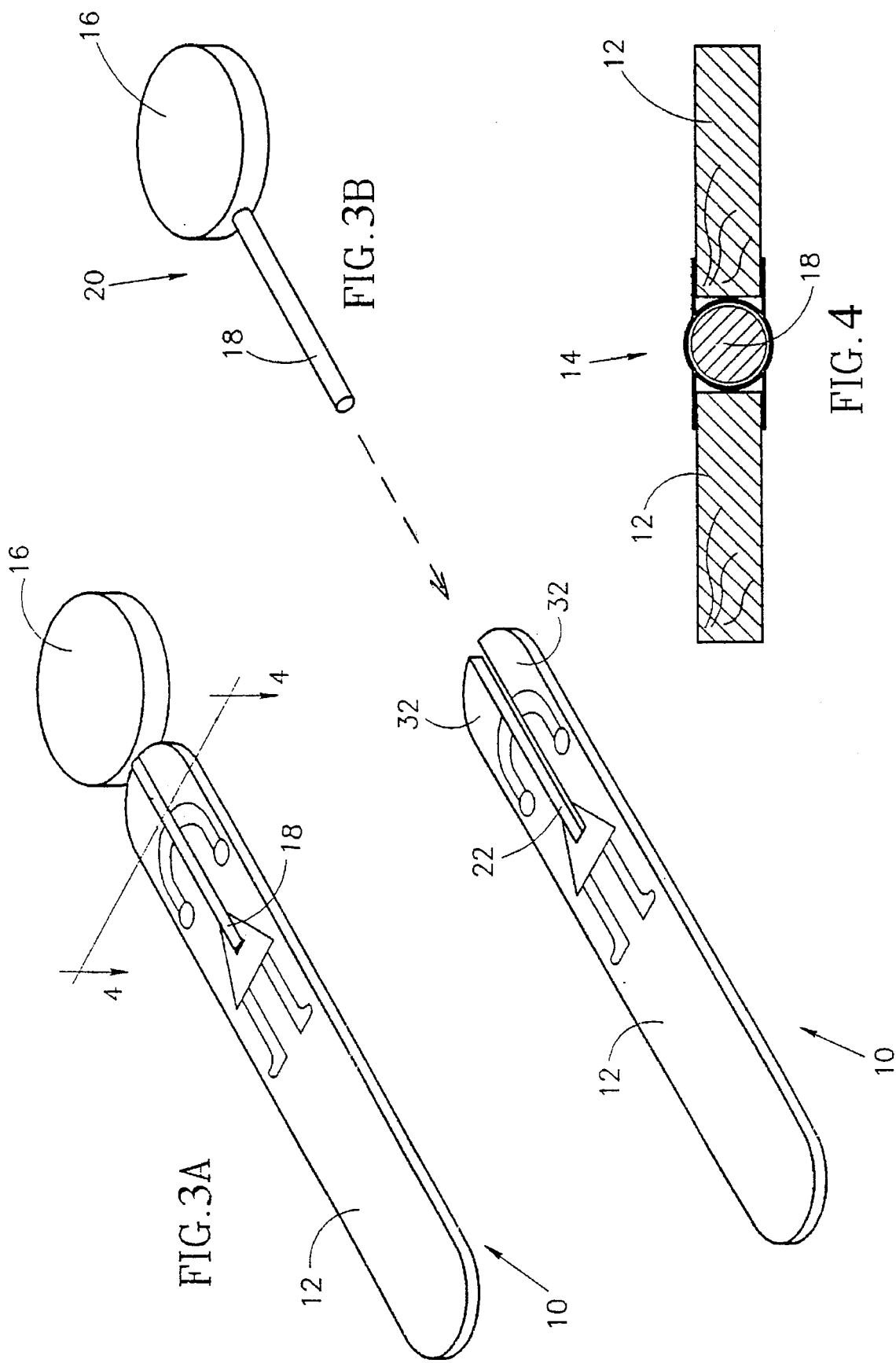

5,634,885

TONGUE DEPRESSOR WITH LOLLIPOP HOLDER

FIELD AND BACKGROUND OF THE INVENTION

The present invention relates to tongue depressors able to hold the standard sized stick of a hard candy confection such as a lollipop.

In the course of a medical examination of a child or infant, the mouth invariably needs to be examined by the practitioner or doctor. Traditionally, a tongue depressor is used to hold the tongue down so that a clear examination of the patient's throat can be made. However, the practitioner or doctor does not always receive the full cooperation of the patient. As an incentive to cooperate, a young patient can be enticed with the potential reward of a candy confection such as a lollipop.

It is well known in the art to combine the functions of a tongue depressor and candy confection. As taught in U.S. Pat. No. 2,425,945, granted to Leach, a small portion of an end of a body member is channeled out creating an opening and a candy confection is molded onto the body member.

In U.S. Pat. No. 2,857,908, granted to Cornfield, a flat, elongated, straight body has molded around it a candy or confection. Openings in the body allow the candy or confection to extend therethrough, thus securing the candy to the body.

In U.S. Pat. No. 3,867,927, granted to Hergott, the candy or confection is molded onto a narrow extension of a blade and subsequently sealed in a transparent enclosure.

Each of the prior art patents mentioned above teaches in some fashion to mold candy or confection to or around a portion of a tongue depressor blade. In each case, the candy or confection is molded directly to the tongue depressor portion during the manufacturing process.

A disadvantage of these prior art inventions is that the candy confection must be molded directly to the tongue depressor. This requires an additional manufacturing step adding to the cost of any product embodying the invention. In addition, the candy or confection is not securely held to the tongue depressor permitting it to fall or break off as the candy or confection is consumed.

Another disadvantage of the prior art inventions is that there is no simple method of replenishing the candy confection portion once the candy confection portion is consumed. Consequently, the tongue depressor will typically be discarded after the candy portion is consumed.

SUMMARY OF THE INVENTION

The present invention overcomes these disadvantages by eliminating the need to mold the candy confection directly to the tongue depressor portion. Instead, the present invention utilizes a holder wherein the stick of a lollipop is inserted into the holder where it is held firmly in place. This reduces the cost of manufacture of any product embodying the present invention. In addition, when the candy or confection portion of the lollipop is consumed, it is a simple matter to remove the remaining stick and replace it with a fresh lollipop.

Hence, there is provided according to the teachings of the present invention, a tongue depressor comprising a blade for restraining the tongue of a patient so as to allow a clearer examination of the rear of the mouth and throat region; and a holder for receiving the stick portion of a lollipop, the holder being detachably connected to one end of the blade.

BRIEF DESCRIPTION OF THE DRAWINGS

The invention is herein described, by way of example only, with reference to the accompanying drawings, wherein:

FIG. 1A is a perspective view of a preferred embodiment of the present invention depicting the elements thereof in assembled form;

FIG. 1B is a perspective view of the embodiment of FIG. 1A depicting the elements thereof in disassembled form;

FIG. 2 is a cross sectional view taken along section line 2—2 of FIG. 1A;

FIG. 3A is a perspective view of another embodiment of the present invention depicting the elements thereof in assembled form;

FIG. 3B is a perspective view of the embodiment of FIG. 3A depicting the elements thereof in disassembled form; and FIG. 4 is a cross sectional view taken along section line 4—4 of FIG. 3A.

DESCRIPTION OF THE PREFERRED EMBODIMENT

The principles and operation of the present invention may be better understood with reference to the drawings and the accompanying description.

Referring to FIGS. 1A and 1B, the present invention discloses a tongue depressor 10 able to hold a lollipop 20 which includes a stick portion 18 with a candy confection portion 16 molded onto a blade 12. Blade 12 has a similar shape and size as that of a conventional tongue depressor typically used by a doctor to examine the back of the mouth or throat of a patient. Blade 12 is typically made of wood but can be any other suitable material such as plastic. In addition, information, such as printing and/or figures can be imprinted, by stamping or by other means, onto one or both surfaces of blade 12.

In a preferred embodiment of the present invention, located at one end of blade 12, is a slot 22 running from one end of blade 12 towards the opposite end of blade 12, defining two separate prongs 32. Slot 22 is appropriately dimensioned to slidably accommodate an elongated member of holder 14 which is inserted therein. In another embodiment of the present invention, a holder is slidable within a channel located at one end of the blade. This channel is created by removing a portion of the thickness of the blade. Another embodiment includes a blade with neither a slot nor a groove. In both these embodiments, the holder includes a clip to allow the holder to be removably fastened to the blade.

Referring to FIG. 1B, in a preferred embodiment, holder 14 is made of a material such as plastic and includes elongated member 30 having a shape complementary to the shape of stick 18 of conventional lollipop 20. The length of holder 14 is sufficient to receive a portion, preferably, the majority of the length of stick 18 of conventional lollipop 20. Running the length of holder 14, on each side of elongated member 30, are a pair of rails 26 integral with, or connected to elongated member 30. Rails 26 on each side of elongated member 30 are spaced apart substantially the thickness of blade 12 and extend outwardly from elongated member 30. Elongated member 30 of holder 14 grips lollipop stick 18 but allows it to slide back and forth upon application of a small amount of force. Another embodiment of the present invention includes a holder that can accommodate a stick of a lollipop having a shape other than circular, such as a square, rectangular or oval shape.

In a preferred embodiment of the present invention, a portion of holder 14 is inserted into slot 22 of blade 12. Holder 14 slides into slot 22 with rails 26 extending over the surface of blade 12 as shown in FIG. 2. Stick 18 of lollipop 20 is inserted into an opening 24 of elongated member 30 of holder 14. Prongs 32 of blade 12 firmly keep holder 14 in place yet allow it to slide back and forth upon application of a small amount of force.

In another embodiment according to the present invention depicted in FIGS. 3A, 3B and 4, holder 14 is omitted and instead, slot 22 is shaped to accommodate stick portion 18 of lollipop 20 directly, as is best seen in FIG. 4. Use of this embodiment obviates the need to use holder 14 as in the basic embodiment but requires the cutting or forming of a slot 22 of blade 12 which is shaped so as to receive stick portion 18 directly.

While the invention has been described with respect to a limited number of embodiments, it will be appreciated that many variations, modifications and other applications of the invention may be made.

What is claimed is:

1. A tongue depressor for restraining a tongue of a patient to allow a clearer examination of the rear of the patient's mouth and throat region capable of holding a stick of a lollipop comprising:
    (a) a blade having two elongated substantially flat surfaces for restraining the tongue of the patient, said blade having a blade cavity; and
    (b) a holder including an elongated member, said elongated member having a cavity for receiving the stick of the lollipop,
said holder detachably connected to an end of said blade such that said blade accommodates said holder within said blade cavity.

2. The tongue depressor as recited in claim 1, wherein said holder is able to firmly hold the stick portion of the lollipop in place yet allow it to slide back and forth therein.

3. The tongue depressor as recited in claim 1, wherein said blade is able to firmly hold said holder in place yet allow it to slide back and forth therein.

4. A tongue depressor for restraining a tongue of a patient to allow a clearer examination of the rear of the patient's mouth and throat region capable of holding a stick of a lollipop comprising:
    (a) a blade having two elongated substantially flat surfaces, said blade having a first end and a second end, said first end for restraining the tongue of the patient, said second end being formed with a blade cavity; and
    (b) a holder including an elongated member, said elongated member having a cavity for accomodating the stick of the lollipop, the stick of the lollipop having an elongate body featuring a distinct cross sectional shape, said holder detachably connected to said blade such that said second end of said blade accommodates said holder within said blade cavity.

5. The tongue depressor as recited in claim 4, wherein said blade cavity is a slot defining a pair of prongs at said second end of said blade, and said holder is detachably connected to said blade such that said second end of said blade accommodates said holder between said pair of prongs.

6. The tongue depressor as recited in claim 4, wherein said cavity of said elongated member features a shape substantially complementary to that of said stick of the lollipop.

7. The tongue depressor as recited in claim 6, wherein said elongated member firmly holds said stick of said lollipop in place, yet allows it to slide back and forth therein.

8. The tongue depressor as recited in claim 4, wherein said holder includes a pair of rails associated with each side of said elongated member.

9. The tongue depressor as recited in claim 8, wherein said rails on said each side of said elongated member are spaced apart substantially the thickness of said blade, such that said blade firmly holds said holder in place, yet allows it to slide back and forth therein.

10. The tongue depressor as recited in claim 4, wherein said blade includes printing on at least one of its said surfaces.

11. The tongue depressor as recited in claim 4, wherein said blade cavity is a channel having at least one opening, and said holder is detachably connected to said blade such that said second end of said blade accommodates said holder within said channel.

12. A tongue depressor for restraining a tongue of a patient to allow a clearer examination of the rear of the patient's mouth and throat region capable of holding a stick of a lollipop, the stick of the lollipop having an elongate body featuring a distinct cross sectional shape, comprising:
    a blade for restraining the tongue of the patient, said blade formed with a slot shaped to accommodate the stick of the lollipop, said slot extending completely through the thickness of said blade.

13. The tongue depressor as recited in claim 12, wherein said slot having a shape substantially complementary to that of said stick, such that said slot firmly holds said stick of said lollipop in place yet allows it to slide back and forth therein.

14. A tongue depressor for holding a stick of a lollipop to allow a clearer examination of the rear of the patient's mouth and throat region, the stick of the lollipop having an elongate body featuring a distinct cross sectional shape, comprising:
    a blade having two elongated substantially flat surfaces, said blade having a first end and a second end, said first end for restraining the tongue of the patient, said second end being formed with a closed channel shaped to accommodate the stick of the lollipop, said closed channel having at least one opening.

* * * * *